United States Patent
Schlichting et al.

(10) Patent No.: US 10,530,781 B2
(45) Date of Patent: Jan. 7, 2020

(54) MEDICAL DEVICE WITH INPUT UNIT

(71) Applicant: Drägerwerk AG & Co. KGaA, Lübeck (DE)

(72) Inventors: Stefan Schlichting, Lübeck (DE); Joshua Abell, Beverly, MA (US)

(73) Assignee: Drägerwerk AG & Co. KGaA, Lübeck (DE)

( * ) Notice: Subject to any disclaimer, the term of this patent is extended or adjusted under 35 U.S.C. 154(b) by 195 days.

(21) Appl. No.: 15/848,274

(22) Filed: Dec. 20, 2017

(65) Prior Publication Data

US 2018/0183808 A1    Jun. 28, 2018

(30) Foreign Application Priority Data

Dec. 22, 2016    (DE) .......................... 10 2016 015 370

(51) Int. Cl.

| H04L 29/06 | (2006.01) |
|---|---|
| G16H 40/67 | (2018.01) |
| G06F 21/44 | (2013.01) |
| G06F 21/41 | (2013.01) |
| H04L 12/24 | (2006.01) |
| H04L 12/26 | (2006.01) |

(52) U.S. Cl.
CPC .......... H04L 63/105 (2013.01); G06F 21/41 (2013.01); G06F 21/445 (2013.01); G16H 40/67 (2018.01); H04L 41/06 (2013.01); H04L 43/0811 (2013.01)

(58) Field of Classification Search
None
See application file for complete search history.

(56) References Cited

U.S. PATENT DOCUMENTS

| 8,464,063 B2 | 6/2013 | Agarwal et al. | |
| 2005/0091539 A1 | 4/2005 | Wang et al. | |
| 2011/0225426 A1* | 9/2011 | Agarwal ................. | G06F 21/41 713/175 |
| 2014/0033303 A1* | 1/2014 | Reggiardo ............. | G16H 40/63 726/21 |
| 2015/0230760 A1* | 8/2015 | Schneider .............. | A61B 90/96 600/300 |

FOREIGN PATENT DOCUMENTS

EP    2 229 876 A1    9/2010

* cited by examiner

*Primary Examiner* — Andrew J Steinle
(74) *Attorney, Agent, or Firm* — McGlew and Tuttle, P.C.

(57) ABSTRACT

A medical device has a device component with an operating state controllable by predefining a predefined value for an operating parameter. A data network interface receives a data message from a central network computer. The data message indicates whether the central network computer is in a blocked state concerning potential user inputs into an input unit of the network computer. The medical device further has an input unit for the potential input of an input value and at least one control unit configured to predefine the predefined value as a function of the input value to the device component as well as to block the input unit for inputs of a user. The control unit is further configured to block the input unit for the input of the input value as a function of the indicated state of the central network computer.

12 Claims, 6 Drawing Sheets

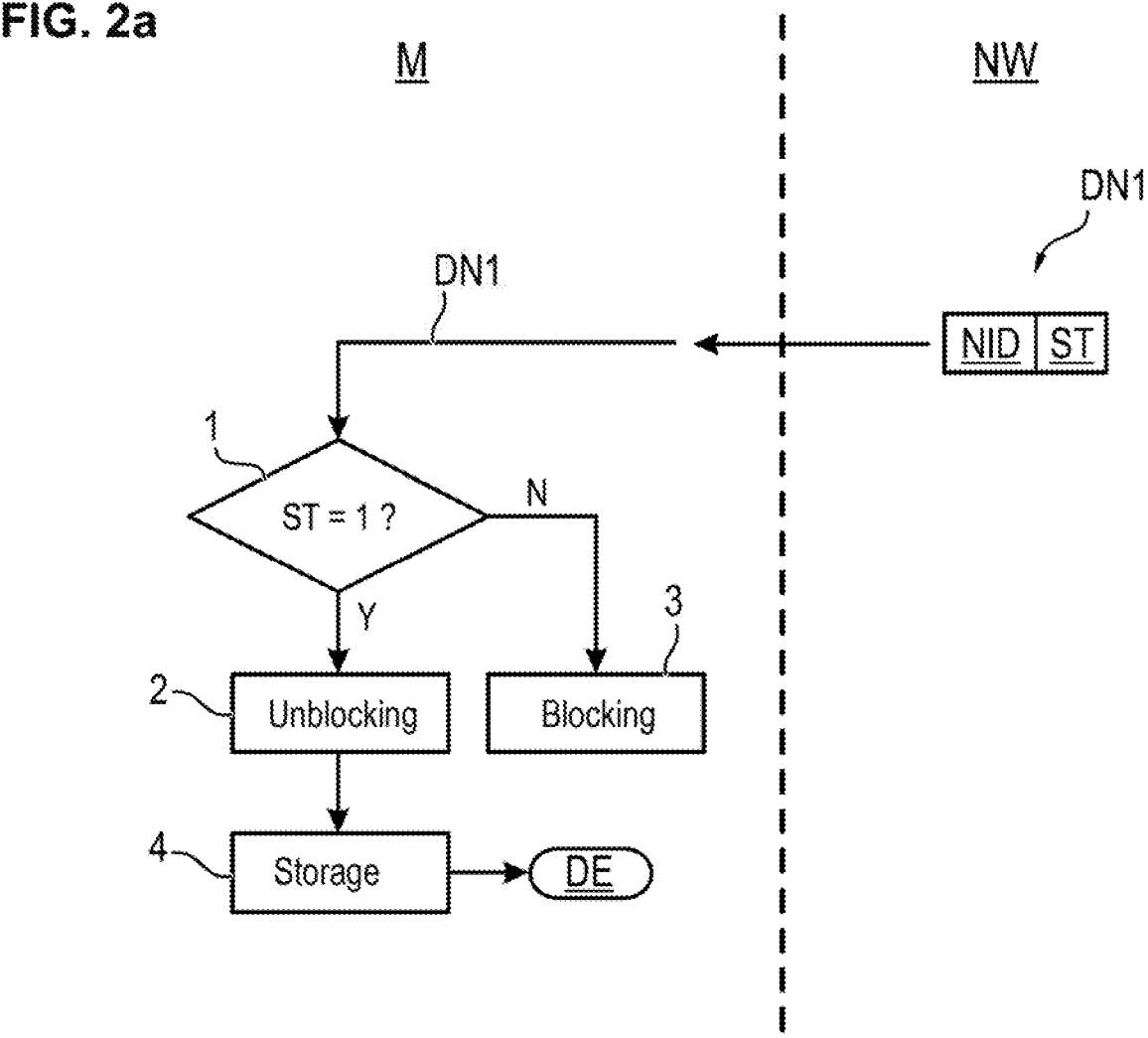

MEDICAL DEVICE WITH INPUT UNIT

CROSS REFERENCE TO RELATED APPLICATIONS

This application claims the benefit of priority under 35 U.S.C. § 119 of German Application 10 2016 015 370.9, filed Dec. 22, 2016, the entire contents of which are incorporated herein by reference.

FIELD OF THE INVENTION

The present invention pertains to medical devices in which a device component for analyzing sensor signals or for physiologically acting on a patient can be adjusted in terms of an operating parameter by inputting an input value into an input unit of the medical device.

BACKGROUND OF THE INVENTION

Medical devices in which a device component for analyzing sensor signals or for physiologically acting on a patient can be adjusted in terms of an operating parameter by inputting an input value into an input unit of the medical device are known from the state of the art. For example, the operating parameter can then be taken into consideration when analyzing the physiological sensor signal or when operating the actuator.

To input input values, users use as an input unit, for example, a so-called touchscreen to input or predefine input values for respective operating parameters by touching certain areas of the touchscreen. Inputs can also be made in this connection via so-called hard keys, such as a keyboard, rotary knobs or other knobs.

Further, medical devices are known, which can be configured via a data network interface. For example, a predefined value for an operating parameter can be transmitted in this case by a central network computer in the form of a data signal via a data network to the data interface of the medical device, so that the medical device then analyzes the data signal and uses the predefined value indicated in it in reference to the operating parameter.

It is conceivable, in principle, in such concepts, in which medical devices can be configured by central network computers, that an operating situation arises, in which predefined values for corresponding operating parameters can be set or predefined simultaneously on both the input unit of the medical device and an input unit of the network computer.

To avoid that an unlimited number of users or unauthorized users can adjust corresponding operating parameters at any time, it is known, in principle, from the state of the art that a user unblocks precisely such a device on an individual device, for example, on a medical device or on a central network computer by inputting authentication data such that the input of input values or predefined values for operating parameters is then possible after the unblocking.

It shall be avoided hereby that an unlimited number of users or unauthorized users can predefine or set values for the operation of the medical device.

If a plurality of medical devices are used to act physiologically on a patient and/or to analyze physiological sensor signals of the patient, it is possible, in principle, that a user authenticates himself at every individual medical device by inputting authentication data each time, so that every individual device is then unblocked such that predefined values for corresponding operating parameters of the medical device can be predefined on a corresponding input unit.

Such a procedure may be very complicated for a clinician or user, because he or she would thus have to authenticate himself or herself at each particular medical device by inputting authentication data each time in order to subsequently also perform corresponding settings for or predefining predefined values related to operating parameters at each particular medical device.

SUMMARY OF THE INVENTION

An object of the present invention is therefore to provide a medical device, in which an input unit of a medical device can be blocked and unblocked for a potential input of input values related to operating parameters, and, in particular, the user's operating effort is minimized.

Furthermore, another possible object of the invention is to document the users, who are cleared for an input unit, in order to identify the users in case of a clinical event.

The medical device according to the present invention has at least one device component, having an operating state that can be controlled by predefining a predefined value for an operating parameter of the device component. The medical device further has a data network interface, for receiving at least one data message from a central network computer. The data message indicates whether the central network computer is in a blocked state in respect to potential user inputs into an input unit of the network computer. The medical device further has a medical device input unit for a potential input of an input value, as well as at least one control unit. The control unit is configured to predefine the predefined value for the device component as a function of the input value as well as to block the input unit for inputs by a user, wherein the control unit is further configured to block the input unit for the input of the input value as a function of the indicated state of the central network computer.

The device component is preferably a device component for analyzing a physiological sensor signal of a patient or a device component for physiologically acting on a patient.

The medical device according to the present invention is advantageous because the input unit does not necessarily have to be unblocked itself by a user by inputting authentication data for a potential input of an input value and hence for controlling a predefined value for an operating parameter.

If the medical device is in a trustworthy data connection or data communication with the central network computer, it is sufficient for a user to also clear or unblock the input unit of the medical device for the input of the input value related to the operating parameters, for example, by corresponding inputs of authentication data on an input unit of the central network computer and, automated hereby, also the input unit of the medical device for the input of the input value, because the unit blocks and unblocks the input unit depending on the indicated state of the central network computer. The authentication data may be data such as, for example, user names, user groups, roles or similar data.

In other words, the control unit blocks the input unit of the medical device for the input of the input value when the data message indicates that the input unit of the central network computer is blocked for user inputs. If the data message indicates that the input unit of the central network computer is unblocked for user inputs, the control unit unblocks the input unit of the medical device for the input of the input value.

As a result, the user does not have to unblock the corresponding input unit at an individual medical device by inputting the authentication data each time on site, but the central network computer can automatically clear different medical devices, which are configured according to the medical device according to the present invention, globally with respect to respective input units for the input of input values.

Consequently, a plurality of medical devices, which are all connected to one and the same patient or are located at the same treatment location, can be cleared by the central network computer for the input of input values together by the central network computer.

The central network computer is, for example, a network device with a network connection via wired transmission technology or a wireless transmission technology (wireless technology). The central network computer may be a stationary network computer or a mobile network computer.

The data message preferably indicates, furthermore, an authorization level of a user of the central network computer, and the control unit is further configured to unblock the input unit for the input of the input value when the indicated authorization level is equal to or higher than a predefined, necessary authorization level. The predefined authorization level is provided here by a memory unit of the medical device.

The medical device is preferably configured such that the at least one device component is an actuator for acting physiologically on a patient, a measuring unit for analyzing at least one physiological sensor signal, or an alarm generation unit for outputting at least one alarm signal on the basis of at least one physiological sensor signal. The control unit is preferably configured to provide a control signal for the device component and to select the control signal as a function of the predefined value.

The medical device is preferably configured such that in case the input unit is blocked by the control unit for the input of the input value, the control unit is configured to configure the input unit such that an input of an unblocking signal into the input unit by a user is possible and to receive the unblocking signal and to unblock the input unit for the input of the input value in the presence of the unblocking signal.

In the sense of this application, an input unit may be an independent input unit, e.g., an independent touchscreen or an independent screen with input means, e.g., rotary knobs, rotary pushbuttons or keys associated with the screen. As an alternative, an input unit may be a certain area of a touchscreen in the sense of a partial screen or of a subscreen. A certain area of such a screen can in this case be blocked or unblocked correspondingly as an input unit according to the present invention, while other areas of such a screen do not represent the input unit according to the present invention and are or can be configured independently from the blocking and unblocking operation according to the present invention.

This embodiment of the medical device according to the present invention is advantageous because even in case the input unit is blocked with respect to potential inputs of input values by the control unit, the user is still able to unblock the input unit for the input of an input value by a separate unblocking signal.

If, for example, the input unit is blocked by the control unit, it may nevertheless be necessary in an emergency for a user not to need to use a central network computer to unblock the input unit of the medical device, because this could be too time-consuming, but the user will prefer to unblock the input unit directly at the medical device by the separate unblocking signal in order to then be able to input on the same input unit an input value, which is then used as a predefined value for an operating parameter of the device component.

An alarm signal is preferably outputted by the control unit in the presence of the unblocking signal. This alarm signal may be transmitted into a data network, for example, in the form of a data message. This unblocking or this intrusion is preferably also documented, e.g., in the form of a file in a data bank on the medical product. An authorized user can preferably mark this entry in the data bank as having been performed by him or her, later when there is no emergency situation any more.

This is advantageous because in the special case in which the user inputs the unblocking signal and thus overrides the blocked state proper of the input unit based on the current configuration of the central network computer, additional network computers are informed by this alarm signal that a user has just inputted the unblocking signal in the medical device or the input unit thereof. The alarm signal is preferably a signal for actuating an optical and/or acoustic alarm output unit, which may be provided at the medical device itself.

The control unit is preferably configured to unblock the input unit for the input of the input value for a predefined time period in the presence of the unblocking signal. The input unit is preferably unblocked only for a predefined time period starting from the presence of the unblocking signal.

The data message preferably indicates, furthermore, an authorization level of a user of the central network computer, and the control unit is configured to select the duration as a function of the indicated authorization level.

This embodiment is advantageous because the input unit should not be unblocked for any desired, unlimited duration possibly by the emergency unblocking of the input unit by the user or by the input of the unblocking signal, because other potential users could possibly be located later in the vicinity of the input unit or of the medical device, and such additional potential users may not be authorized to input values for adjusting operating parameters on the medical device. This is avoided by the predefined duration.

The control unit is preferably configured to prolong the predefined duration in the presence of a request signal of the user at the input unit. This embodiment is advantageous because the user may not be able to perform all the necessary settings or inputs of input values within the predefined time period, but requires a longer time period for this. This is made possible for him by the possibility of inputting the request signal and the prolongation of the duration, which results therefrom.

The data message, which indicates the authorization level, preferably also contains an additional optional data element, which indicates a predefined duration. This duration may either be inputted by a user on the central computer or predefined from a data table on the central computer.

The control unit is preferably configured to store, furthermore, a data element in a memory unit of the medical device in the presence of the unblocking signal, wherein the data element indicates the process of unblocking the input unit. The data element preferably also indicates the time of unblocking the input unit. This is advantageous because it can be documented hereby in the memory unit whether the input unit was unblocked and the time at which it was unblocked. The data element preferably indicates, furthermore, an identity of a user, who performed the unblocking.

The medical device is preferably configured such that the memory unit is configured to provide certificate data and further to check the authenticity of the central network computer on the basis of the certificate data as well as on the basis of data messages exchanged via the data interface with the central network computer.

This embodiment is advantageous because the medical device can check as a result the authenticity of the central network computer in order to then block or unblock its own input unit depending on whether the central network computer is in the unblocked state.

The medical device is preferably configured such that the memory unit is further configured to provide authentication data of a user, and the control unit is further configured to determine, on the basis of data messages exchanged with the network computer via the data interface, whether there currently is a data network connection to the central network computer, and if there is currently no data network connection to the central network computer, to configure the input unit such that a user can input authentication data into the input unit and can receive the authentication data, and to unblock the input unit for the input of the input value if a comparison of the authentication data provided with the authentication data inputted by the user in the input unit is positive.

This embodiment is advantageous because the medical device or its memory unit can thus determine whether a data network connection to the central network computer is currently indeed present, and the memory unit can put the medical device into a default operating parameter if this data connection is currently no longer present. It is still possible in this default operating parameter that the user can unblock the input unit of the medical device for the input of the input value related to the operating parameter by inputting authentication data.

The medical device is preferably configured such that the control unit is further configured to derive a user identity from the authentication data provided and/or from the inputted authentication data and to make known the user identity by means of a data message provided at the data interface.

This embodiment is advantageous because the identity of the user who unblocked the input unit for the input of input values related to operating parameters by inputting authentication data is thus made known to other network computers of the network.

The medical device is preferably configured such that the control unit is further configured to determine on the basis of data messages exchanged via the data interface with the central network computer whether a data network connection to the central network computer is currently present and to output an alarm in case there currently is no data network connection to the central network computer.

This embodiment is advantageous because in case the alarm signal is a data signal, it is made possible hereby for other network computers to be informed that the network connection between the central computer and the medical device does not currently exist any more.

In case the alarm signal is a signal for actuating an alarm output unit for outputting an optical and/or acoustic alarm signal at the medical device itself, a user located in the area of the medical device can be alerted to the fact that the data network connection between the central network computer and the medical device is currently no longer present.

The present invention will be explained in more detail below on the basis of special embodiments without limitation of the general inventive idea on the basis of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 2a is a flow diagram showing possible method steps to be carried out by a control unit of the medical device;

DESCRIPTION OF THE PREFERRED EMBODIMENTS

Figure 1:
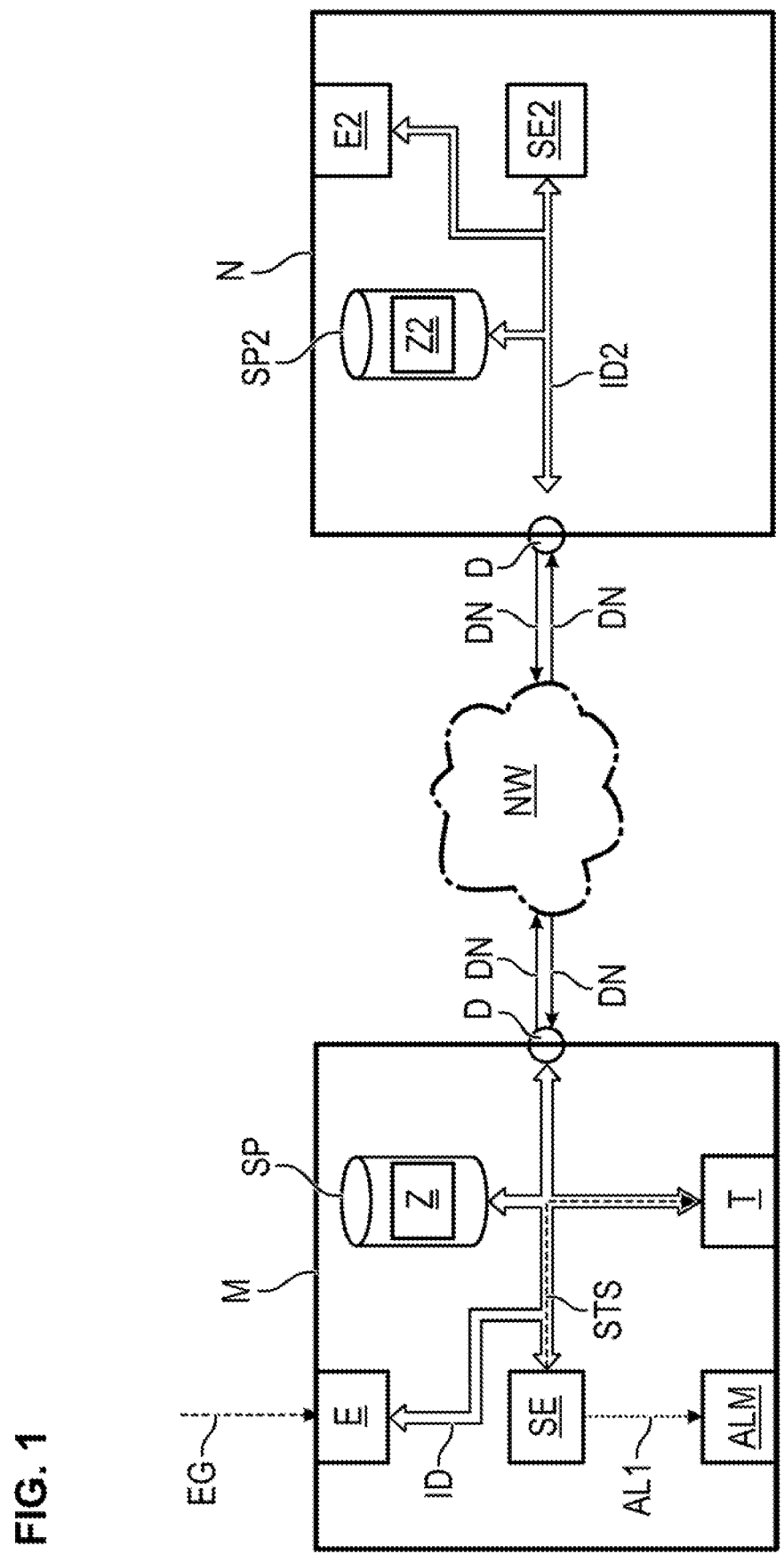
FIG. 1 is a schematic view showing a medical device according to the present invention as well as a central network computer.

Referring to the drawings, FIG. 1 shows the medical device according to the present invention, which has a data network interface D, an input unit E, a control unit SE as well as a device component T. The medical device M preferably also has a memory unit SP. The memory unit SP preferably provides certification data or certificate data Z.

An internal data bus ID preferably connects the unit components SE, T, SP, E, D of the medical device M to one another for internal data transmission.

The medical device M can receive data messages DN from a data network NW and also send such data messages thereto via the data interface D.

A central network computer N has a control unit SE2 as well as an input unit E2. The network computer N preferably has, furthermore, a memory unit SP2 as well as certification data or certificate data Z2. The central network computer N can also exchange data messages DN via a data network NW via a data network interface D.

The unit components E2, SE2, SP2, D of the central computer N are preferably connected to one another via a corresponding internal data bus ID2.

It may happen, for example, that the input unit E2 of the network computer N is a so-called touchscreen, and that a user then unblocks this input unit E2 by inputting identification data and/or authentication data into the input unit E2.

It may then be possible that the input unit E2 permits the input of input values for use concerning operating parameters of the medical device M, in which case the input values can be transmitted, for example, in the form of data messages DN to the medical device M.

The medical device M and the network computer N are associated with one another in the clinical area of the data network NW. The communication between these two computers M, N may take place in an encrypted form, for example, on the basis of certificates or certificate data Z, Z2. The medical device M can derive as a result an authentication of the network computer N.

If, for example, the memory unit SP provides certification data or certificate data Z, the control unit SE can check the authenticity of the network computer N on the basis of the data messages DN by an exchange of data messages DN, so that a state of network computer or of the input unit E2 thereof can securely be taken into consideration for blocking or unblocking the input unit E of the medical device M.

Figure 4A:
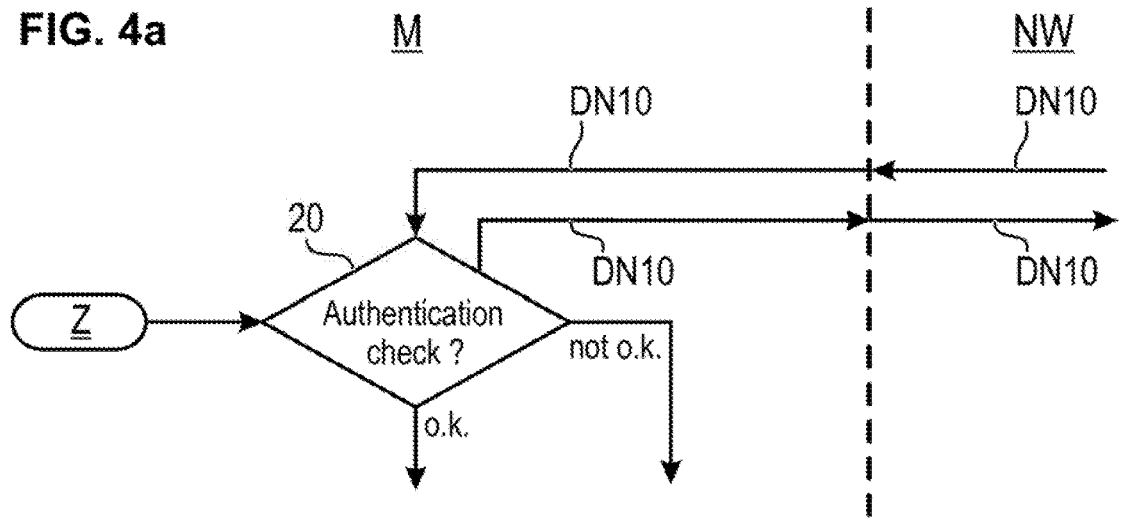
FIG. 4a is a flow diagram showing possible method steps to be carried out by a control unit of the medical device.

FIG. 4a shows for this as an example a step 20, in which the control unit SE, may be connected with the certificate data Z2 of the network computer N from FIG. 1. The control unit SE, on the basis of data messages DN10, can then check the authenticity of the central network computer N on the basis of the certificate data Z from the memory unit SP as well as of the contents of the data messages DN10.

If the control unit SE has unblocked the input unit E for the input of input values, and if corresponding input values are then inputted by a user, these can then be used to control the operating state of the device component T and to predefine the input values as a predefined value for an operating parameter related to the device component T. This is preferably brought about by the control unit SE providing a control signal STS for the device component T and by the control unit SE selecting the control signal STS as a function of the predefined value.

Figure 5A:
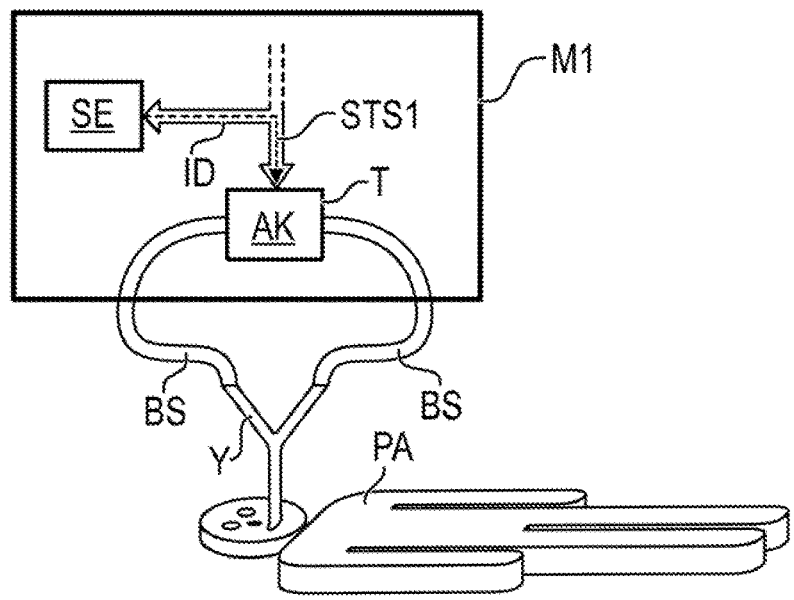
FIG. 5a is a schematic view showing a preferred embodiment of the medical device according to the present invention with various device components.

FIG. 5a shows a first preferred embodiment M1 of the medical device M from FIG. 1.

The device component T is an actuator AK in this case, which is, for example, a gas delivery unit, wherein the actuator is configured to act physiologically on a patient PA. For example, the actuator AK may directly or indirectly be in connection as a gas delivery unit with a breathing organ of the patient PA via ventilation tubes BS and a Y-piece. An example of an operating parameter is a predefined pressure value for a pressure-controlled ventilation.

Figure 5B:
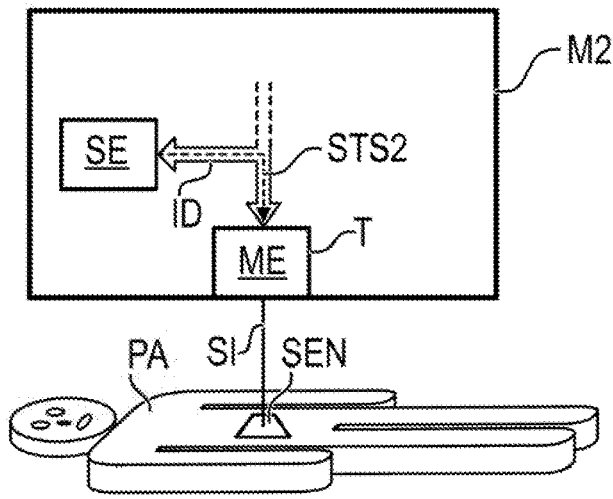
FIG. 5b is a schematic view showing a preferred embodiment of the medical device according to the present invention with different device components.

FIG. 5b shows another embodiment of the medical device M2 according to the present invention. Sensor signals SI, which are analyzed by a measuring unit MG of the medical device M2, are provided here by a sensor SEN. For example, a predefined value related to a parameter is then predefined by means of a control signal STS2 for analysis or signal processing of the physiological sensor signal SI.

Figure 5C:
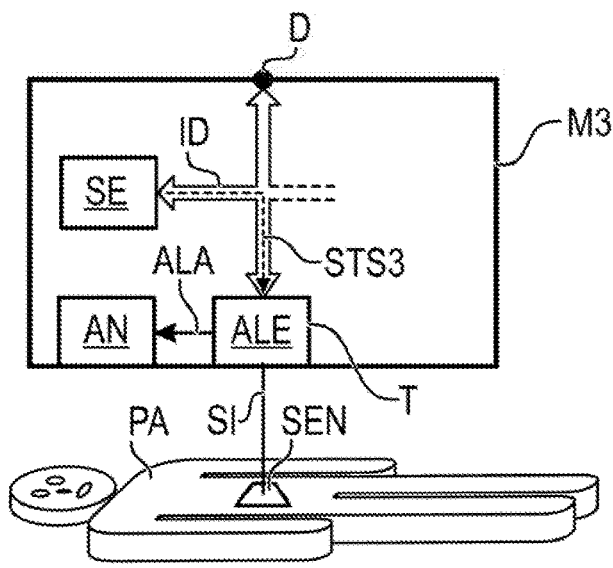
FIG. 5c is a schematic view showing a preferred embodiment of the medical device according to the present invention with different device components.

FIG. 5c shows another preferred embodiment of the medical device MG according to the present invention, wherein the device component is an alarm generation unit ALE, which is configured for output by means of an alarm signal ALA on the basis of the at least one physiological sensor signal SI.

For example, a predefined value related to a threshold value may be predefined here by the control signal STS3 for an alarm generation function of the alarm generation unit ALG.

The alarm generation signal ALA may be outputted, for example, to an alarm output unit AN of the medical device M3.

The alarm output unit AN may be an acoustic and/or optical signal output unit to output an optical and/or acoustic output to a user in the area surrounding the medical device M3.

The alarm generation signal ALA is preferably outputted in the form of a data signal via the data network interface D of the medical device M3.

It can be stated in summary that the control unit SE is configured in all three preferred embodiments to provide a control signal STS1, STS2, STS3 for a device component T, AK, ME, ALE and to select the control signal STS1, STS2, STS3 as a function of the predefined value, which is selected by the control unit as a function of the input value.

The measuring unit ME and/or the alarm generation unit ALE may be components consisting of hardware and/or software in one form of implementation, which are preferably implemented integrally in the control unit SE. The control signals STS2, STS3 are now internal data signals within such a combined unit in such a case.

FIG. 2a shows steps that can be carried out by the control unit SE of the medical device M according to FIG. 1 or by the control units SE from FIGS. 5a through 5c of the corresponding medical devices M1, M2, M3.

A data message DN1, which preferably indicates the network identity NID of the central network computer N, is received via the data network interface. The data message DN1 further has a data element ST, which indicates whether the central network computer is in a blocked state in respect to potential user inputs into the input unit E2 of the network computer N from FIG. 2.

Furthermore, the data element ST preferably indicates which user or which user group has possibly performed the unblocking of the input unit E2 of the network computer N.

The medical device M receives the data message DN1 via the network NW.

A check is performed in a first step 1 to determine whether the input unit of the central network computer is unblocked. This is the case, for example, when the data element ST assumes the value 1.

If the input unit of the central network computer is blocked, the process is branched off to a step 3, in which the input unit of the medical device is blocked for the input of input values related to operating parameters for the device component.

If the input unit of the central network computer is not blocked, but unblocked, the process is branched off to a step 2, in which the input unit of the medical device is unblocked for an input of an input value related to the operating parameter for the device component.

A data element DE, which indicates the unblocking process of the input unit, is then preferably stored in a subsequent step 4 in a memory unit of the medical device. The time of unblocking is preferably also indicated here by the data element DE. The data element DE preferably indicates, moreover, the user who has unblocked the input unit.

It is then possible after the unblocking in step 2 for a user to input an input value into the input unit E from FIG. 1, for example, by an input signal EG, after which the control unit then selects a predefined value for being predefined for the device component T as a function of the input value. The operating state of the device component T is consequently controllable hereby in respect to an operating parameter.

Figure 2B:
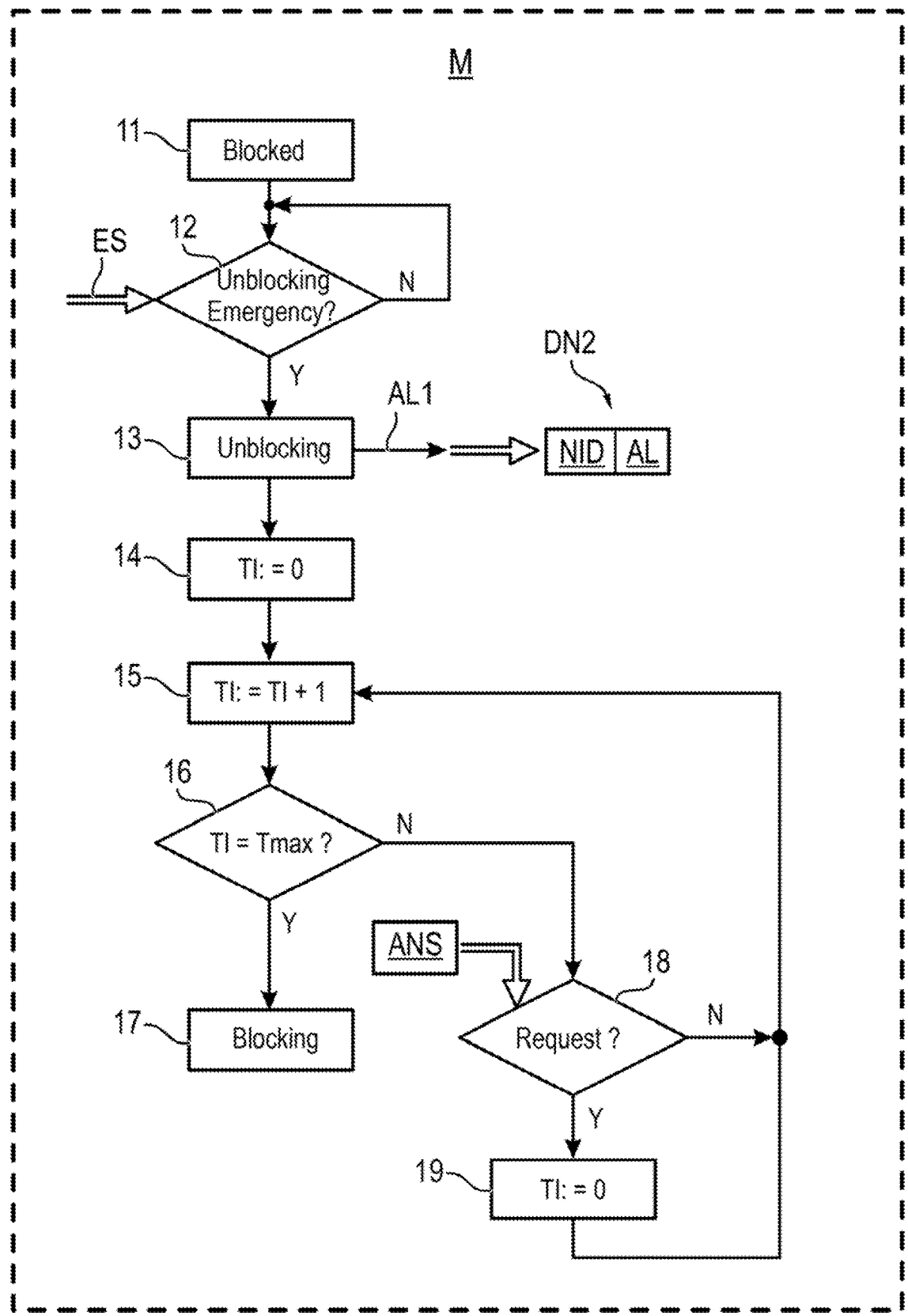
FIG. 2b is a flow diagram showing possible method steps to be carried out by a control unit of the medical device.

FIG. 2b shows additional preferred steps, which can be carried out by the control unit SE of the medical device M from FIG. 1.

It should be assumed that the input unit E of the medical device M, which input unit is shown in FIG. 1, is blocked in a step 11. This happens based on the corresponding blocked state of the input unit E2 of the network computer N from FIG. 1.

If the user would nevertheless like to unblock the input unit E of the medical device M in an emergency for the input of input values related to operating parameters of a device component, he or she can input a corresponding unblocking signal ES in a step 12 according to FIG. 2b.

Figure 3A:
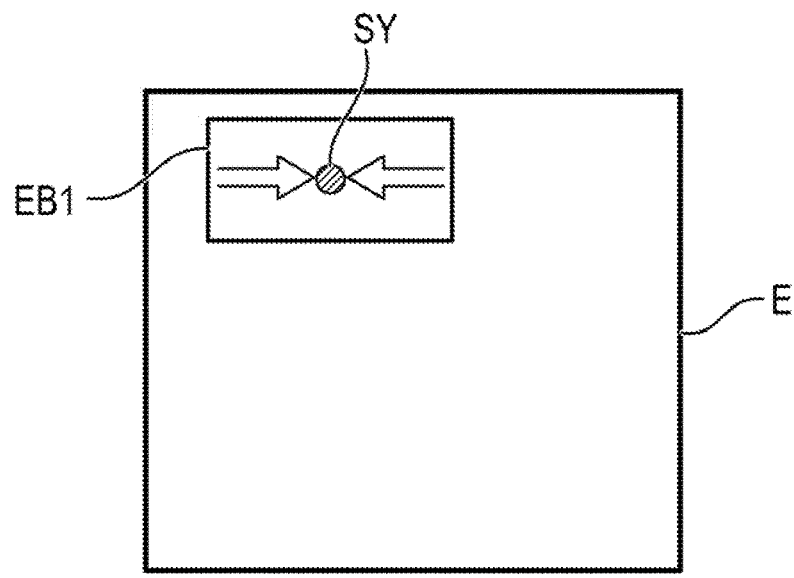
FIG. 3a is a schematic view showing a possible configuration of an input unit of a medical device.

FIG. 3a shows for this the input unit E with a corresponding input area, wherein a symbol SY, which can be touched by a user, for example, on a touchscreen, is shown in a separate input area EB1. This symbol SY may represent a so-called unblocking signal, because the input unit E detects the touching of the symbol or of the corresponding input area of the input unit E and then provides the unblocking signal for the control unit.

Consequently, if the presence of the unblocking signal ES is detected in step 12 according to FIG. 2b, the process is branched off to a step 13, in which the input unit E of the medical device M from FIG. 1 is unblocked for the input of an input value or of at least one input value.

Figure 3B:
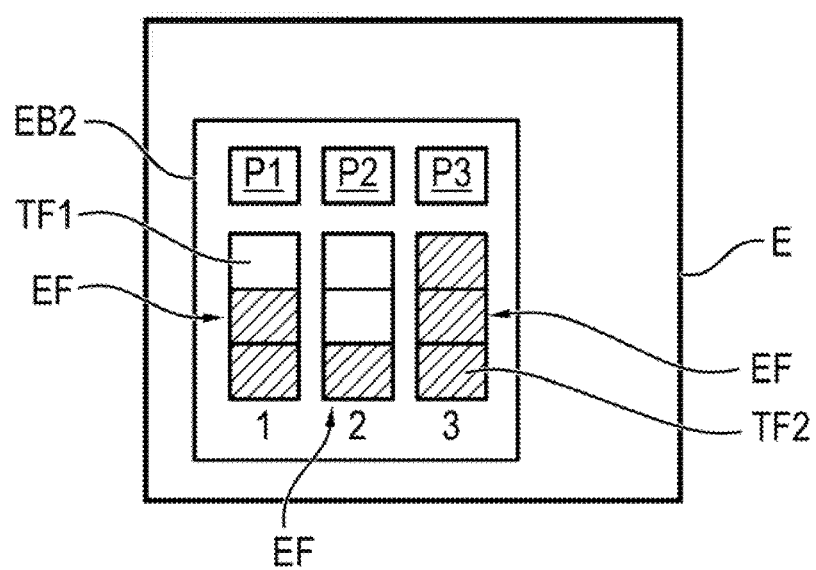
FIG. 3b is a schematic view showing a possible configuration of an input unit of a medical device.
Figure 3C:
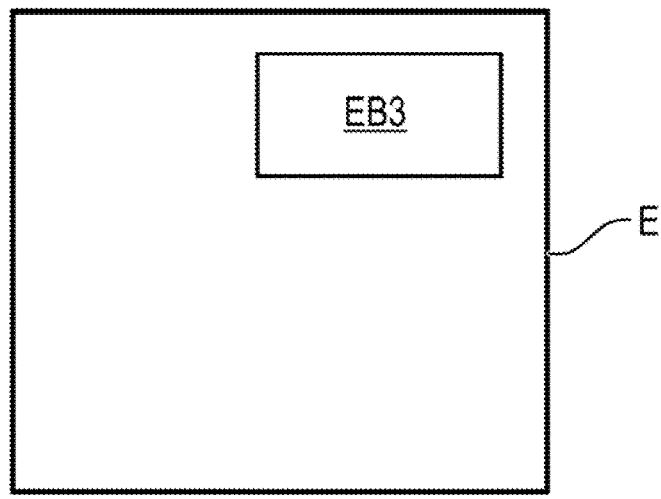
FIG. 3c is a schematic view showing a possible configuration of an input unit of a medical device.

FIG. 3b shows for this such a state of unblocking of the input unit E as an example.

For example, corresponding input fields EF, which are assigned to corresponding parameters P1, P2, P3, may be present in an input area EB2. Corresponding set values are now located under these input fields EF.

The corresponding input fields EF have so-called component fields TF1, TF2. If a user touches a corresponding component field TF1 in the input area EB2, for example, a corresponding input value ,3' related to the operating parameter P1 can then be inputted hereby. For example, an input value ,1' related to the operating parameter P3 can likewise be inputted by touching the component field TF2.

An alarm signal AL1 is then preferably outputted by the control unit SE in step 13 according to FIG. 2b. The alarm signal AL1 is preferably an alarm generation signal for an internal alarm generation unit ALM of the medical device M from FIG. 1.

As an alternative, the alarm generation signal may be a data message DN2, which is provided by the control unit at the data network interface D. The data message DN2 may preferably have in this case as an alarm generation signal a network identity NID of the medical device as well as a data element AL indicating the alarm generation case.

The input unit is preferably unblocked in this case for a predefined duration Tmax only. A timer TI can then be set to 0, for example, in a step 14.

This timer TI is then incremented in a next step 15.

It can then be checked in a step 16 whether the predefined duration has already expired because the timer TI has reached the maximum value Tmax. If yes, the process is branched off to a step 17, in which the input unit E from FIG. 1 is then blocked again by the control unit SE for inputs EG related to input signals or input values.

If the predefined duration has not yet expired, the process is branched off to a step 18. The predefined duration can then preferably be prolonged by a request input ANS by a user into the input unit E according to FIG. 1. This can be brought about, for example, by the process being branched off from step 18 to a step 19, in which the timer TI is again set to the start value 0.

If, however, there is no request input ANS, the process can be branched off further from step 18 to step 15, in which the timer TI is then incremented again.

For example, certificate data Z can be provided, for example, in a step 20 according to FIG. 4a. Data messages DN10, which can be exchanged via the data interface D with the central network computer beyond the network NW, can then be used to check the authenticity of the central network computer on the basis of the certificate data Z and further of the exchanged data messages DN10.

Figure 4B:
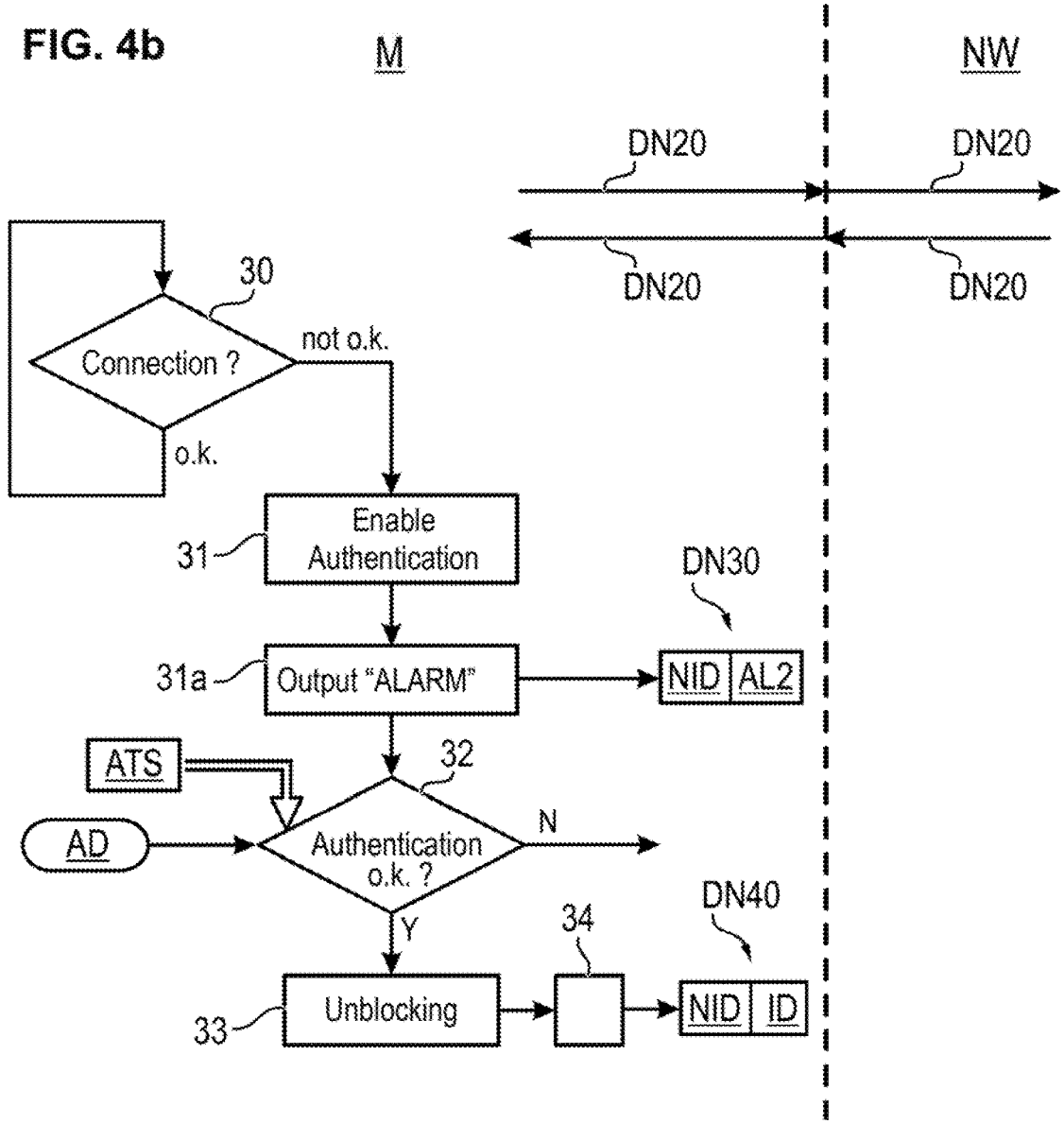
FIG. 4b is a flow diagram showing possible method steps to be carried out by a control unit of the medical device.

According to FIG. 4b, data messages DN20, which can be exchanged with the central network computer via the data network NW, can be taken into consideration in a step 30. If the current data network connection is in order, the process remains in step 30.

If it is determined in step 30 that there currently is no data network connection to the central network computer, the process can then be branched off to a step 31, in which a user can authenticate himself.

An alarm signal, which is provided in the form of a data signal DN30, is then preferably outputted in a step 31a. The data signal DN30 preferably has the network identity NID of the medical device as well as a data element AL2, which indicates the presence of the alarm generation state.

Identification data AD of a user is then provided from the memory unit SP of the medical device M according to Figure a step 32. Further, authentication data ATS may be taken into consideration by the input unit, for example, in the form of an input signal ATS. If a comparison of the authentication data AD provided with the given authentication data ATS is positive (Y), the input unit is then unblocked in a step 33. The user identity of the user, who has performed the authentication and has thus brought about the unblocking, is then preferably derived in a step 34 from the provided authentication data AD and/or the inputted authentication data ATS. This user identity is then made known by means of a data message DN40 provided at the data interface D of the medical device M according to FIG. 1. The data message DN40 preferably has to this end the network identity NID of the medical device as well as the user identity ID.

Depending on certain implementation requirements, exemplary embodiments of the present invention may be implemented in hardware and/or in software. In particular, a control, a measuring unit or an alarm generation unit may be implemented in hardware and/or in software in the sense of this application. A control unit, a measuring unit or an alarm generation unit may be implemented by a respective individual hardware component or else by a respective system of hardware components. The implementation may be carried out with the use of a digital storage medium, for example, a floppy disk, a DVD, a Blu-Ray disk, a CD, a ROM, a PROM, an EPROM, an EEPROM or a FLASH memory, a hard drive or another magnetic or optical memory, on which electronically readable control signals, which can interact or do interact with a programmable hardware component such that the respective method is carried out, are stored.

A programmable hardware component may be formed by a processor, a computer processor (CPU=Central Processing Unit), a graphics processor (GPU=Graphics Processing Unit), a computer, computer system, an application-specific integrated circuit (ASIC=Application-Specific Integrated Circuit), a single-chip system (SOC=System on Chip), a programmable logic element field-programmable gate array with a microprocessor (FPGA=Field Programmable Gate Array).

The digital storage medium may therefore be machine- or computer-readable. Some exemplary embodiments consequently comprise a data storage medium, which has electronically readable control signals, which are capable of interacting with a programmable computer system or with a programmable hardware component such that one of the methods being described here is executed. An exemplary embodiment is thus a data storage medium (or a digital storage medium or a computer-readable medium), on which the program is recorded for executing a method being described here.

Exemplary embodiments of the present invention may generally be implemented a program, firmware, computer program or computer program product with a program code or as data, wherein the program code or the data acts/act such as to execute one of the methods when the program is running on a processor or on a programmable hardware component. The program code or the data may also be stored on a machine-readable storage medium or data storage medium. The program code or the data may be present, among other things, as a source code, machine code or byte code as well as another intermediate code.

Further, another exemplary embodiment data stream, a signal sequence or a sequence of signals, which represents/represent the program for executing one of the methods being described here. The data stream, the signal sequence or the sequence of signals may be configured, for example, such as to be transferred via data communication connection, for example, via the internet or another network. Exemplary embodiments are thus also signal sequences, which represent data and which are suitable for transmission via a network or a data communication connection, wherein the data represent the program.

A program according to one exemplary embodiment may implement one of the methods during its execution, for example, by reading storage locations or writing a datum or a plurality of data into these, as a result of which switching operations or other procedures are brought about in transistor structures, in amplifier structures or in other electrical, optical, magnetic components or components according to another principle of operation. Data, values, sensor values or other information may correspondingly be detected, determined or measured by a program by reading a storage location. A program may therefore detect, determine or measure variables, values, measured variables and other information by reading one or more storage locations as well as bring about, prompt or execute an action by writing to one or more storage locations as well as actuate other devices, machines and components.

The above-described exemplary embodiments represent only an illustration of the principles of the present invention. It is obvious that modifications and variations of the arrangements and details being described here will be seen by other persons skilled in the art. The present invention is therefore intended to be limited only by the scope of protection of the following patent claims rather than by the specific details that were presented here on the basis of the description and the explanation of the exemplary embodiments. While specific embodiments of the invention have been shown and described in detail to illustrate the application of the principles of the invention, it will be understood that the invention may be embodied otherwise without departing from such principles.

What is claimed is:

1. A medical device comprising:
   at least one device component having an operating state that can be controlled by predefining a predefined value for an operating parameter, wherein the at least one device component comprises an actuator for physiologically acting on a patient, a measuring unit for analyzing at least one physiological sensor signal or an alarm generation unit for outputting at least one alarm signal on the basis of at least one physiological sensor signal or any combination of the actuator, the measuring unit and the alarm generation unit;
   a data network interface for receiving at least one data message from a central network computer, wherein the data message indicates a state of the central network computer as to whether the central network computer is in a blocked state concerning potential user inputs into a network computer input unit of the network computer;
   an input unit for receiving a potential input of an input value;
   a control unit comprising one or more processors, the control unit being configured:
      to predefine the predefined value as a function of the input value to the device component;
      to block the input unit as to inputs of a user;
      to block the input unit as to the input of the input value as a function of the indicated state of the central network computer;
      to block the input unit for the input of the input value when the data message indicates that the input unit of the central network computer is blocked for user inputs;
      to provide a control signal for the at least one device component and to select the control signal as a function of the predefined value;
      to configure the input unit in case the input unit is blocked by the control unit for the input of the input value such that an input of an unblocking signal into the input unit by a user is possible and to receive the unblocking signal, if any; and
      to unblock the input unit for the input of the input value in the presence of the unblocking signal.

2. A medical device in accordance with claim 1, wherein the control unit is further configured to unblock the input unit for the input of the input value when the data message indicates that the input unit of the central network computer is unblocked for user inputs.

3. A medical device in accordance with claim 1, wherein:
   the data message further indicates an authorization level of a user of the central network computer; and
   the control unit is further configured to unblock the input unit for the input of the input value when the indicated authorization level is equal to or higher than a predefined, necessary authorization level.

4. A medical device in accordance with claim 1, wherein the control unit is further configured to unblock the input unit for the input of the input value for a predefined duration in the presence of the unblocking signal.

5. A medical device in accordance with claim 4, wherein:
   the data message further indicates an authorization level of a user of the central network computer, and
   the control unit is further configured to select the duration as a function of the indicated authorization level.

6. A medical device in accordance with claim 4, wherein the control unit is further configured to prolong the predefined duration in the presence of a request input of the user into the input unit.

7. A medical device in accordance with claim 1, wherein the control unit is configured to output an alarm signal in the presence of the unblocking signal.

8. A medical device in accordance with claim 1, further comprising a memory unit, wherein the control unit is further configured to store a data element, which data element indicates the operation of unblocking of the input unit, in the memory unit in the presence of the unblocking signal.

9. A medical device in accordance with claim 1, wherein:
the memory unit is configured to provide certificate data; and
the control unit is configured to check an authenticity of the central network computer on the basis of the certificate data and, furthermore, on the basis of data messages exchanged with the network computer via the data interface.

10. A medical device in accordance with claim 9, wherein
the memory unit is further configured to provide authentication data of a user;
the control unit is further configured:
to determine on the basis of data messages exchanged with the central network computer via the data interface whether a data network connection to the central network computer is currently present;
and if there is currently no data network connection to the central network computer,
to configure the input unit such that an input of authentication data by a user into the input unit is possible and to potentially receive the authentication data; and
further, if a comparison of the provided authentication data with authentication data inputted by the user into the input unit is positive, to unblock the input unit for the input of the input value.

11. A medical device in accordance with claim 10, wherein the control unit is further configured:
to derive a user identity from the provided authentication data and/or the inputted authentication data; and
to make the user identity known by means of a data message provided at the data interface.

12. A medical device according to claim 1, wherein the control unit is further configured:
to determine on the basis of data messages exchanged with the network computer via the data interface whether a data network connection to the central network computer is currently present; and
to output an alarm signal in the form of a data signal, in case no data network connection to the central network computer is currently present.

* * * * *